United States Patent
Fujita et al.

(10) Patent No.: US 9,472,386 B2
(45) Date of Patent: Oct. 18, 2016

(54) CHROMATOGRAPH MASS SPECTROMETRY DATA PROCESSING APPARATUS

(71) Applicant: SHIMADZU CORPORATION, Kyoto-shi, Kyoto (JP)

(72) Inventors: Yuichiro Fujita, Kyoto (JP); Shigeki Kajihara, Uji (JP)

(73) Assignee: SHIMADZU CORPORATION, Kyoto (JP)

( * ) Notice: Subject to any disclaimer, the term of this patent is extended or adjusted under 35 U.S.C. 154(b) by 416 days.

(21) Appl. No.: 14/177,302

(22) Filed: Feb. 11, 2014

(65) Prior Publication Data
US 2014/0303903 A1    Oct. 9, 2014

(30) Foreign Application Priority Data

Apr. 4, 2013    (JP) .................................. 2013-078428

(51) Int. Cl.
*H01J 49/00*  (2006.01)
*G01N 30/86*  (2006.01)
*G01N 30/72*  (2006.01)

(52) U.S. Cl.
CPC ........... *H01J 49/0036* (2013.01); *G01N 30/86* (2013.01); *G01N 30/72* (2013.01); *G01N 30/8675* (2013.01)

(58) Field of Classification Search
CPC ... H01J 49/0036; G01N 30/86; G01N 30/72; G01N 30/8675
USPC ........... 702/23, 27, 32, 28, 30, 76, 173, 189; 250/255, 339.12; 436/173, 174, 63; 356/301; 324/310, 312
See application file for complete search history.

(56) References Cited

U.S. PATENT DOCUMENTS 5,175,430 A * 12/1992 Enke .................. G01N 30/8679
                                                            250/282
7,982,181 B1 *  7/2011 Senko .................... G01N 30/72
                                                            250/281

(Continued)

FOREIGN PATENT DOCUMENTS

JP    2008241721 A    10/2008
WO   2013001618 A1    1/2013

OTHER PUBLICATIONS

Ken Aoshima et al., "AB3D: A suite of Algorithms for Biomarker Discovery in Diagnostics and Drug Development using LC-MS" Summary of 56th Annual Conference on Mass Spectrometry, 2008, pp. 520-521.
Communication dated May 31, 2016, from the Japanese Patent Office in counterpart application No. 2013-078428.

*Primary Examiner* — Carol S Tsai
(74) *Attorney, Agent, or Firm* — Sughrue Mion, PLLC (57) ABSTRACT

Even when only mass spectra wherein the reproducibility of peak intensities is low are obtained in a mass spectrometry apparatus using, for example, a MALDI ion source, the correction of shifts in retention time using TICs for a plurality of specimens is performed with good precision. For each mass spectrum, variable scaling is executed which combines such first scaling as to equalize the extent of variations in signal intensity values in one mass spectrum, among different mass spectra, and second scaling for performing weighting according to relative variations in signal intensity values for each mass spectrum (S3). The signal intensity values after the scaling are added to obtain a total signal intensity value for one measurement time point (S4). From a plurality of total signal intensity values thus obtained, a TIC is created (S6). Using these TICs, RT alignment is executed (S8). Thus, the similarity in TIC waveforms increases, and RT alignment can be suitably performed.

4 Claims, 8 Drawing Sheets

(56) References Cited

U.S. PATENT DOCUMENTS

| | | | |
|---|---|---|---|
| 9,287,105 B2* | 3/2016 | Kawaguchi | H01J 49/26 |
| 2006/0255258 A1* | 11/2006 | Wang | G01N 30/8624 |
| | | | 250/282 |
| 2011/0101215 A1* | 5/2011 | Hirabayashi | G01N 30/8675 |
| | | | 250/282 |
| 2013/0228677 A1* | 9/2013 | Kawaguchi | H01J 49/26 |
| | | | 250/281 |
| 2013/0289893 A1* | 10/2013 | Kawase | H01J 49/0036 |
| | | | 702/23 |
| 2014/0012515 A1* | 1/2014 | Taneda | G06F 19/708 |
| | | | 702/32 |
| 2014/0132607 A1* | 5/2014 | Kawana | G06T 11/206 |
| | | | 345/440 |
| 2014/0156203 A1* | 6/2014 | Yamaguchi | G01N 30/8655 |
| | | | 702/23 |
| 2014/0244185 A1* | 8/2014 | Yamamura | H01J 49/0036 |
| | | | 702/23 |
| 2014/0303903 A1* | 10/2014 | Fujita | H01J 49/0036 |
| | | | 702/23 |
| 2014/0324362 A1* | 10/2014 | Andersson | H01J 49/0036 |
| | | | 702/28 |

* cited by examiner

Fig. 5A WITHOUT RT ALIGNMENT

| Name of identified protein | RANK | Score | Number of identified peaks | Number of peaks in which $p < 0.05$ holds as a result of u-test, among identified peaks |
|---|---|---|---|---|
| ALBU_BOVIN | 4 | 369 | 33 (20) | 30 (19) |
| ENO1(2)_YEAST | 1 | 555/439 | 24 (11) | 1 (1) |
| ADH1_YEAST | 2 | 496 | 29 (13) | 0 (0) |
| PYGM_RABIT | 3 | 376 | 56 (25) | 6 (4) |
| HBA_BISBO/HBB_BOVIN | 5,6 | 122/95 | 17 (9) | 0 (0) |

Fig. 5B ONLY RT ALIGNMENT (WITHOUT SCALING)

| Name of identified protein | RANK | Score | Number of identified peaks | Number of peaks in which $p < 0.05$ holds as a result of u-test, among identified peaks |
|---|---|---|---|---|
| ALBU_BOVIN | 4 | 307 | 32 (21) | 27 (21) |
| ENO1(2)_YEAST | 1 | 524/432 | 25 (11) | 1 (1) |
| ADH1_YEAST | 2 | 472 | 29 (14) | 2 (1) |
| PYGM_RABIT | 3 | 352 | 52 (24) | 11 (9) |
| HBA_BISBO/HBB_BOVIN | 5,6 | 95/59 | 13 (9) | 0 (0) |

Fig. 5C SCALING + RT ALIGNMENT BY METHOD OF PRESENT INVENTION

| Name of identified protein | RANK | Score | Number of identified peaks | Number of peaks in which $p < 0.05$ holds as a result of u-test, among identified peaks |
|---|---|---|---|---|
| ALBU_BOVIN | 3 | 294 | 21 (20) | 21 (20) |
| ENO1(2)_YEAST | 1 | 471/394 | 15 (10) | 1 (1) |
| ADH1_YEAST | 2 | 354 | 19 (13) | 1 (1) |
| PYGM_RABIT | 4 | 208 | 30 (23) | 2 (1) |
| HBA_BISBO/HBB_BOVIN | 5,6 | 66/59 | 7 (7) | 0 (0) |

Fig. 6A  WITHOUT RT ALIGNMENT (BEFORE ALIGNMENT)

Fig. 6B  WITH RT ALIGNMENT

CHROMATOGRAPH MASS SPECTROMETRY DATA PROCESSING APPARATUS

TECHNICAL FIELD

The present invention relates to a chromatograph mass spectrometry data processing apparatus for processing mass spectrometry data obtained by a chromatograph mass spectrometer in which a chromatograph, such as a liquid chromatograph or a gas chromatograph, and a mass spectrometer are combined.

BACKGROUND ART

In recent years, chromatograph mass spectrometry combining chromatography and mass spectrometry is widely used in various fields, such as medicines, pharmaceuticals, food, and environment. There are various analysis methods for data obtained by chromatograph mass spectrometry. One of them is differential analysis in which difference among the data of two or more groups is examined An example of the differential analysis is an analysis processing for finding a specific protein that is not seen in a non-patient and is seen only in a cancer patient (that is, a biomarker for the cancer disease). In chromatograms and mass spectrums, peaks that are not present in the group of biological samples taken from a plurality of non-patients and are present in the group of biological samples taken from a plurality of cancer patients are searched.

A procedure for the above differential analysis using a liquid chromatograph mass spectrometry apparatus will be outlined.

First, one or a plurality of proteins contained in a sample taken from a subject (non-patients or patient) are broken down into a plurality of peptides with a digestive enzyme to obtain a mixture of peptides. Next, the peptide mixture is introduced into a liquid chromatograph to separate the peptides according to their own retention times. Every specimen thus separated according to the retention time containing a peptide is measured by a mass spectrometry apparatus to obtain data in which the signal intensities of ions derived from the peptide are included.

Figure 7:
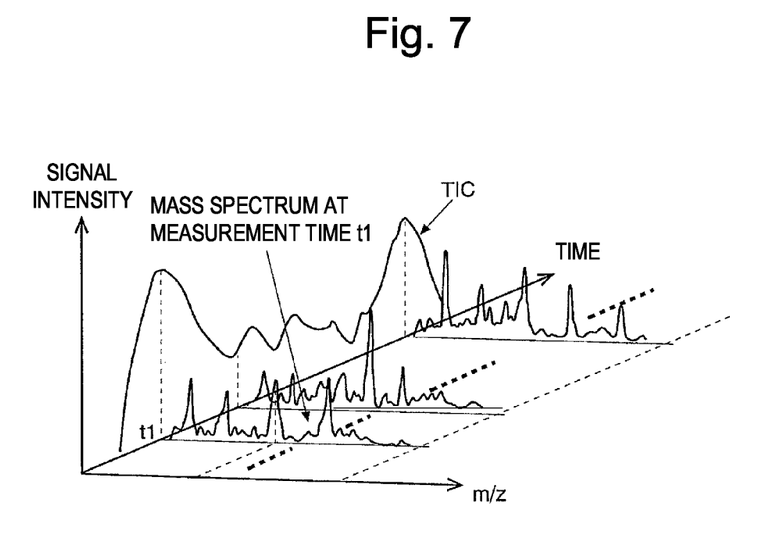
FIG. 7 is a schematic diagram of three-dimensional chromatogram data and a TIC obtained by a liquid chromatograph mass spectrometry apparatus.

FIG. 7 is a schematic diagram of three-dimensional chromatogram data obtained in this manner. That is, data obtained by a liquid chromatograph mass spectrometry apparatus is a collection of data of a signal intensity (intensity of ions) at a certain time and a certain mass-to-charge ratio m/z.

A peak corresponding to a particular peptide appears at a retention time (RT) corresponding to the peptide and a mass-to-charge ratio m/z corresponding to the peptide. In other words, the position of a peak derived from a peptide is represented by [RT, m/z] coordinates, or a two-dimensional vector of the two components. Therefore, in order to examine whether or not a peptide is present in a certain sample group, one can examine whether or not a peak corresponding to the peptide is present at the position [RT, m/z] . However, generally, the reproducibility of chromatogram data (that is, reproducibility in the time direction) is lower than the reproducibility of mass spectrum data (that is, reproducibility in the mass-to-charge ratio direction). Therefore, for the same substance, the retention time of the corresponding peak may be different depending on the sample, the analysis conditions, or other factors.

Thus, generally, before actually searching for a difference in peaks among a plurality of groups, correction in the time axis is performed within each group and further among the groups, so that mass spectrum peaks derived from the same substance appear at the same retention time position. One method for such correction is "RT alignment using TICs" in which correction is performed using total ion chromatograms (TICs) obtained by plotting along time the sum of signal intensity values in a mass spectrum at each measurement time point.

In the following description, unless particularly described, "RT alignment using TICs" is simply referred to as "RT alignment." In other words, "RT alignment" means "RT alignment using TICs" in the present specification.

When a liquid chromatograph and a mass spectrometry apparatus are used in combination, an ion source by atmospheric pressure ionization, such as electrospray ionization (ESI) or atmospheric pressure chemical ionization (APCI), is often used. Generally, the reproducibility of mass spectra obtained in such a liquid chromatograph mass spectrometry apparatus is high, and for the same peptide, peak having substantially the same signal intensity is obtained. Therefore, the reproducibility of the waveform of TICs is also high, and the similarity in the waveform of a plurality of TICs obtained for specimens of the same type is high.

Making use of such similarity in the waveform of TICs, chromatogram peaks are corrected in the time axis by RT alignment using a known algorithm, such as dynamic programming (DP) so that the TIC waveform of a sample designated as "Treatment" is as close as possible to the TIC waveform of a sample designated as "Control." In addition, at this time, the analyst changes parameters, such as the calculation conditions of dynamic programming, variously and visually compares the TIC waveform of the Treatment and the TIC waveform of the Control after the correction, and searches for the most appropriate parameters (that is, such parameters that the positions of the peaks and the waveforms in the two TICs are closest in terms of time). Thus, good RT alignment can be achieved.

For example, in Non-Patent Document 1, RT alignment by dynamic programming using a correlation coefficient is disclosed. One example of the results of actually performing RT alignment using this technique is shown in FIG. 8.

Figure 8:
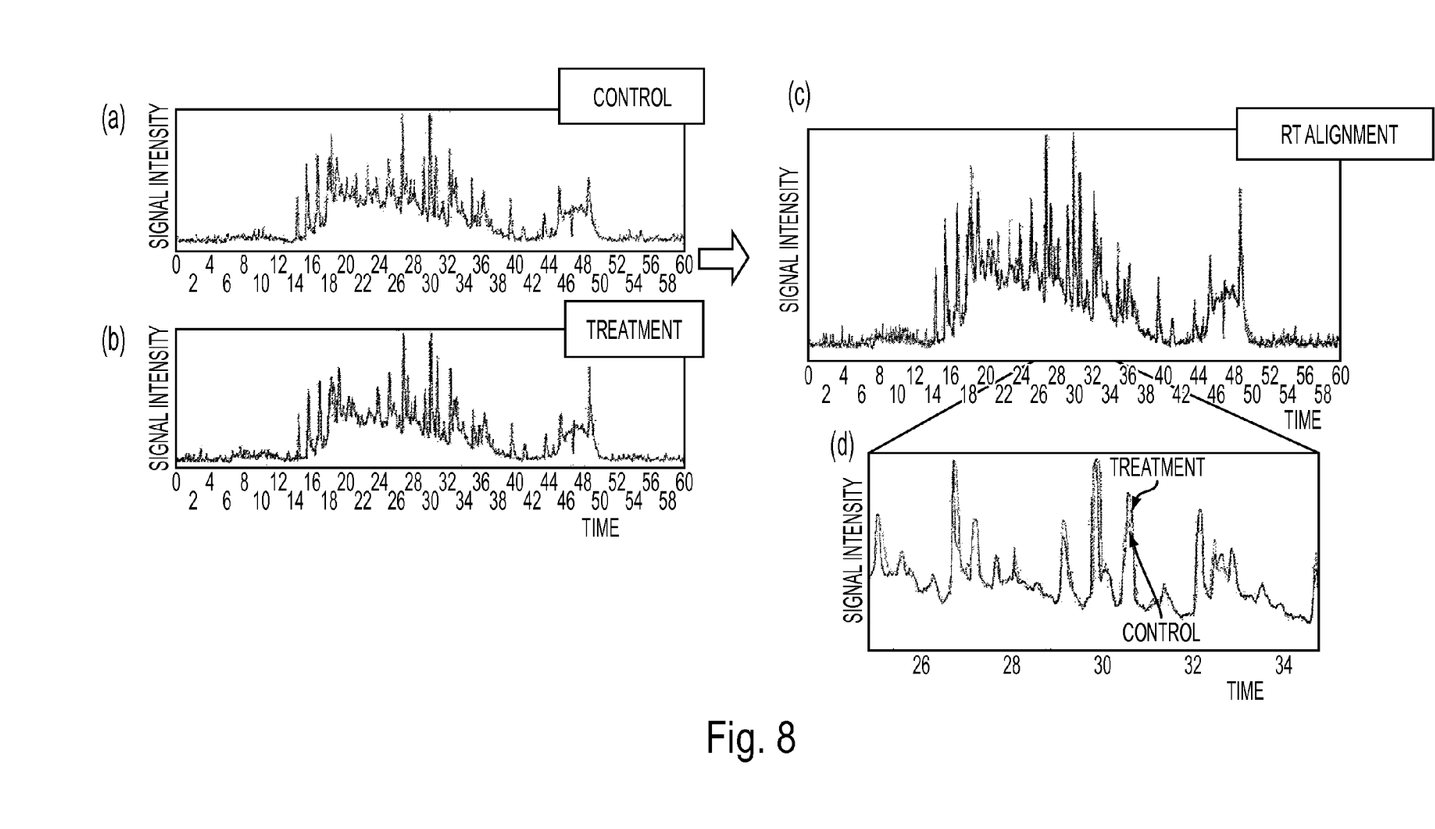
FIG. 8 shows one example of the results of executing RT alignment on data obtained by a liquid chromatograph mass spectrometry apparatus using an ESI ion source.

FIG. 8(a) is the TIC of a sample designated as Control, and FIG. 8(b) is the TIC of a sample designated as Treatment. A graph in which the TIC of the Control and the TIC of the Treatment after RT alignment are overlap-displayed is shown in FIG. 8(c). In addition, a graph in which the time range around 25 to 35 minutes in FIG. 8(c) is enlarged is shown in FIG. 8(d). From this diagram, it is found that the positions of the peak tops and the peak bottoms, the peak widths, and the like in both TIC waveforms match quite well. In other words, in this case, it can be said that the RT alignment is performed with good precision.

But, according to the study of the inventors of this application, it has become clear that the above-described RT alignment method is suitable for three-dimensional chromatogram data acquired by a liquid chromatograph mass spectrometry apparatus using an ion source by ESI or the like, but is not suitable for three-dimensional chromatogram data acquired by a liquid chromatograph mass spectrometry apparatus using an ion source by matrix-assisted laser desorption ionization (MALDI). The reason is thought to be as follows.

The RT alignment by dynamic programming or the like described above presumes that the similarity in the waveform of a plurality of TICs (for example, the TICs of Control and Treatment) to be aligned is rather high, and the similarity of the TICs are increased by shifting the retention times of peaks around areas in which the match between the TIC waveforms is low, or by other measures. However, in a MALDI ion source, variations in the amount of ions produced for one laser pulse irradiation are large, and the reproducibility of ion production efficiency for each mass-to-charge ratio is not very good. Therefore, in mass spectra obtained by a MALDI mass spectrometry apparatus, the reproducibility of the signal intensities of peaks is low, and the reproducibility of a total signal intensity value at a certain measurement time point obtained by adding all signal intensity values for each mass spectrum is also low. As a result, the similarity in TIC waveform among different samples is also poor. Among TICs having poor similarity in this manner, even if dynamic programming can be executed, retention times cannot be suitably corrected.

In addition, as described above, whether or not the RT alignment is successful is judged by the analyst visually checking the overlap display of TICs as shown in FIGS. 8(c) and 8(d). For this purpose, at the stage before retention times are corrected, the similarity in the two TIC waveforms must be high to a certain extent. But, when a MALDI ion source is used as described above, the similarity in the TIC waveforms among different samples is poor. Therefore, even if overlap display is performed, it is difficult for the analyst to visually determine whether or not the RT alignment is properly executed. In addition, therefore, the optimal adjustment of parameters for dynamic programming is also difficult.

BACKGROUND ART DOCUMENT

Patent Document

[Non-Patent Document 1] Ken Aoshima, Satoshi Tanaka, seven others, "AB3D: A suite of Algorithms for Biomarker Discovery in Diagnostics and Drug Development using LC-MS" Summary of the 56th Annual Conference on Mass Spectrometry, 2008, pp. 520-521

DISCLOSURE OF THE INVENTION

Problems to be Solved by the Invention

The present invention is made in view of such respects, and it is a main object of the present invention to provide a chromatograph mass spectrometry data processing apparatus that can appropriately correct, with good precision, retention times in TICs created based on data collected, for example, by a liquid chromatograph mass spectrometry apparatus using a MALDI ion source.

Means for Solving the Problems

The present invention made in order to solve the above problem is a chromatograph mass spectrometry data processing apparatus for processing data collected by a chromatograph mass spectrometry apparatus, the data processing apparatus performing alignment processing for correcting a shift in retention time in a plurality of chromatograms obtained from data obtained for a plurality of specimens, and including:

a) a mass spectrum scaling processing unit for scaling signal intensities in a mass spectrum created, for each measurement time point within an entire measurement time range or within a part of the measurement time range, based on data obtained at the measurement time point;

b) a total signal intensity value calculation unit for calculating, for each of the mass spectrum, a total signal intensity value obtained by adding signal intensity values after being scaled by the mass spectrum scaling processing unit;

c) a chromatogram creating unit for creating, for each of a plurality of specimens, a total ion chromatogram (TIC) from a plurality of total signal intensity values calculated by the total signal intensity value calculation unit; and d) an alignment execution unit for executing alignment processing using a plurality of chromatograms created by the chromatogram creating unit.

In data processing, such as spectrum analysis, the scaling of peaks or the like is one of generally used techniques. It is exclusively performed as preprocessing for comparing peaks with each other, or is performed for comparing the tendency of the entire waveform. On the other hand, in the chromatograph mass spectrometry data processing apparatus according to the present invention, scaling is not applied to a plurality of waveforms, TIC waveforms in this case, to be compared. Instead, scaling is applied to a waveform composed of a large number of original data points for obtaining data points constituting such a waveform, i.e. a mass spectrum in this case. Then, by adding a large number of signal intensity values modified by the scaling in one mass spectrum, one total signal intensity value corresponding to the mass spectrum is calculated.

As described above, for example, in a mass spectrometry apparatus using a MALDI ion source, the reproducibility of peak signal intensities appearing in mass spectra is not good, and even for the same substance, a relatively large difference occurs in the signal intensities of peaks in different mass spectra. The total signal intensity value obtained by adding signal intensity values appearing in one mass spectrum is likely to be affected by peaks having high signal intensity values appearing in the mass spectrum, and the large difference in the signal intensity values of such peaks among a plurality of samples is a major factor of decreasing similarity in TICs. On the other hand, it can be said that such difference or variation in signal intensity value are some of the general properties of mass spectra, and therefore, scaling in response to the difference or variation is also necessary.

Therefore, as one aspect of the chromatograph mass spectrometry data processing apparatus according to the present invention, the above mass spectrum scaling processing unit can be constituted of variable scaling combining first scaling and second scaling, where the first scaling is for equalizing or at least reducing an extent of variations in signal intensity values in one mass spectrum, among different mass spectra, and the second scaling is for performing weighting according to relative variations in signal intensity values for each mass spectrum.

The above first scaling can be, for example, a processing for dividing the signal intensity value of any peak in the mass spectrum by the standard deviation of the signal intensity values of peaks (usually a plurality of peaks) in the mass spectrum, or a processing for dividing the signal intensity value of any data point by the standard deviation of the signal intensity values of any data point in the mass spectrum. This means aligning the extent of variations in signal intensity values among a plurality of mass spectra. The above second scaling can be, for example, processing for dividing the signal intensity value of any peak or any data point in the mass spectrum by a coefficient of variation (=[standard deviation]/[average value]) obtained from the signal intensity values of peaks or any data points in the mass spectrum, in other words, multiplying by the reciprocal of the coefficient of variation as weight. This means reflecting relative difference among mass spectra with regard to variations in signal intensity values in one mass spectrum.

As another aspect of the chromatograph mass spectrometry data processing apparatus according to the present invention, the above mass spectrum scaling processing unit may perform scaling processing for taking logarithms of signal intensities of peaks in one mass spectrum.

In the chromatograph mass spectrometry data processing apparatus according to the present invention, the chromatogram creating unit creates a chromatogram, that is, a TIC, in a predetermined time range from a plurality of total signal intensity values for different measurement time points calculated based on scaled signal intensity values. This TIC is created for each specimen to be subjected to differential analysis or the like. The alignment execution unit executes alignment processing using a plurality of TICs created by the above chromatogram creating unit, and corrects shifts in retention time so that chromatogram peaks derived from the same substance appear at substantially the same time. The alignment processing method is not limited, and conventionally used various methods, such as dynamic programming, can be used.

By the characteristic scaling as described above for a mass spectrum, the influence of a peak having a particularly high signal intensity in the mass spectrum on a total signal intensity value decreases, and thus, the low reproducibility of peak intensities in mass spectra is less likely to be brought into a TIC. As a result, the similarity in the waveforms of TICs in a plurality of specimens on which alignment processing is to be executed increases, and alignment processing can be suitably executed, and the retention times of peaks for the same substance can be aligned. In addition, since the similarity in TIC waveforms in a plurality of specimens on which alignment processing is to be executed increases, it is also easy for an analyst to visually check these waveforms and determine whether or not the alignment processing is properly executed. Further, also for parameter adjustment for performing alignment processing, such as dynamic programming, the analyst can perform easily and appropriately while visually checking the TIC waveforms.

Effects of the Invention

According to the chromatograph mass spectrometry data processing apparatus according to the present invention, even when the reproducibility of peak intensities is low as in mass spectra acquired by a liquid chromatograph mass spectrometry apparatus using a MALDI ion source, it is possible to create, for a plurality of specimens, TICs in which the similarity in waveform among them is high, and perform, using these TICs, suitable alignment processing so that chromatogram peaks derived from the same substance appear at the same time. In addition, the similarity in the waveforms of TICs for a plurality of specimens increases, and therefore, an analyst can visually judge success or failure of alignment processing. Since parameter adjustment for the alignment processing is also possible, the precision of RT alignment is further enhanced. When the precision of RT alignment is improved in this manner, for example, the precision of differential analysis for a plurality of specimens can be improved.

MODES FOR CARRYING OUT THE INVENTION

One embodiment of a liquid chromatograph mass spectrometry system including a data processing apparatus according to the present invention is described below with reference to the accompanying drawings.

Figure 1:
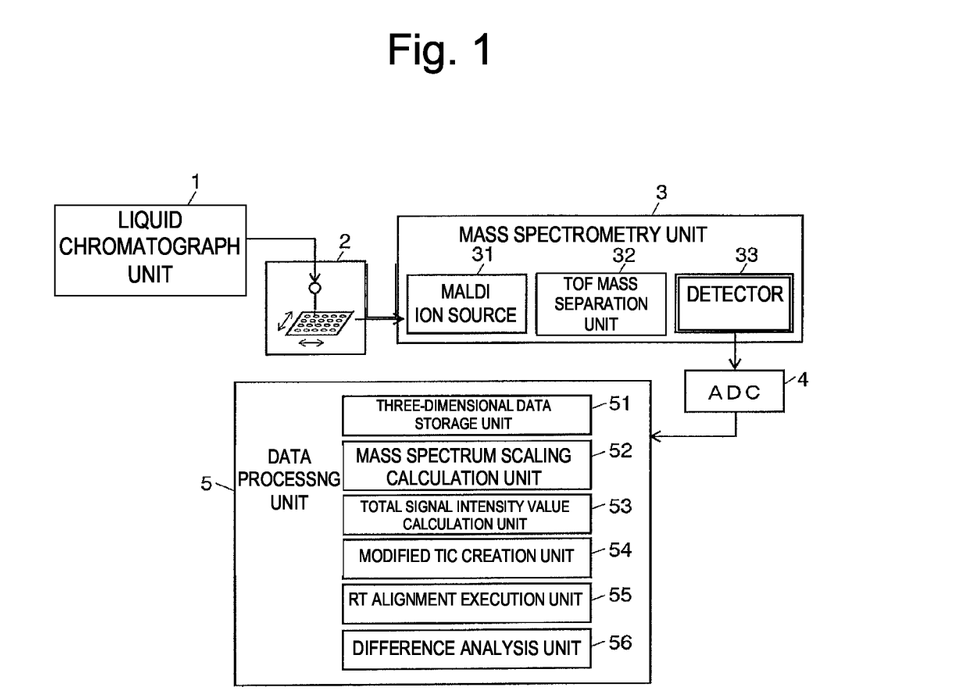
FIG. 1 is a schematic block diagram of one embodiment of a liquid chromatograph mass spectrometry system including a chromatograph mass spectrometry data processing apparatus according to the present invention.

FIG. 1 is a schematic block diagram of the liquid chromatograph mass spectrometry system in this embodiment.

In FIG. 1, a liquid chromatograph unit 1 includes an injector that introduces a specimen solution into a mobile phase flowing at a constant flow rate, and a column that separates various substances contained in the specimen in the time direction, though they are not shown. Various substances appear sequentially with the lapse of time in an eluate eluted from the outlet of the column. A spotting unit 2 fractionates this eluate at predetermined time intervals, mixes the fractionated eluate and a matrix, and drops the mixture onto a sample plate for MALDI to prepare each fractionated specimen. In other words, different fractionated specimens contain substances in the eluate eluted from the column at different time points.

A mass spectrometry unit 3 includes a MALDI ion source 31, a time-of-flight (TOF) mass separation unit 32, and a detector 33. The MALDI ion source 31 irradiates one fractionated specimen on the sample plate with laser beam to ionize the substance contained in the fractionated specimen. The produced ions are introduced into the TOF mass separation unit 32, and the ions are separated according to the mass-to-charge ratio while flying in a flight space having a predetermined length. The detector 33 detects the ions arriving in a state of being separated according to the mass-to-charge ratio, and outputs a detection signal according to the amount of the arriving ions. The detection signal obtained in the detector 33 is converted to digital data in an analog-digital converter (ADC) 4, and input to a data processing unit 5. The position of the sample plate is scanned in the MALDI ion source 31, and then, mass spectrometry on a large number of fractionated specimens formed on the plate is sequentially executed.

The data processing unit 5 includes functional blocks, such as a three-dimensional data storage unit 51, a mass spectrum scaling calculation unit 52, a total signal intensity value calculation unit 53, a modified TIC creation unit 54, an RT alignment execution unit 55, and a differential analysis unit 56. The data which is input to the data processing unit 5 through the analog-digital converter 4 as described above is time-of-flight spectrum data showing the relationship between the time of flight and signal intensity (ion intensity) with reference to a certain time point (for example, a time point when a fractionated specimen is irradiated with laser beam in the MALDI ion source 31). In the data processing unit 5, calibration data showing the relationship between the time of flight and mass-to-charge ratio m/z is stored. Based on this calibration data, the time of flight is converted to a mass-to-charge ratio, and stored in the three-dimensional data storage unit 51 as mass spectrum data showing the relationship between mass-to-charge ratio and signal intensity.

The function of the data processing unit 5 can also be implemented using a dedicated hardware, but is generally implemented by using a common personal computer as hardware resources, and executing a dedicated processing software installed in the personal computer.

In the liquid chromatograph mass spectrometry system in this embodiment, the eluate continuously eluted from the liquid chromatograph unit 1 is fractionated for each predetermined time to provide different fractionated specimens, and for each of the fractionated specimens, mass spectrum data over a predetermined mass-to-charge ratio range is obtained. Therefore, when one mass spectrum for one fractionated specimen is arranged in the order of the time series in which the fractionated specimen is obtained, three-dimensional chromatogram data as shown in FIG. 7 is obtained. When differential analysis on a plurality of specimens is performed, the chromatograph mass spectrometry is executed for each specimen as described above to acquire three-dimensional chromatogram data as shown in FIG. 7.

Now, here, it is assumed that for two specimens, a specimen A and a specimen B, to be subjected to differential analysis, three-dimensional chromatogram data is already acquired, and stored in the three-dimensional data storage unit 51. The data processing unit 5 executes RT alignment processing on the data according to the flowchart shown in FIG. 2 to align the retention times of chromatogram peaks for the same substance, and then executes differential analysis.

Figure 2:
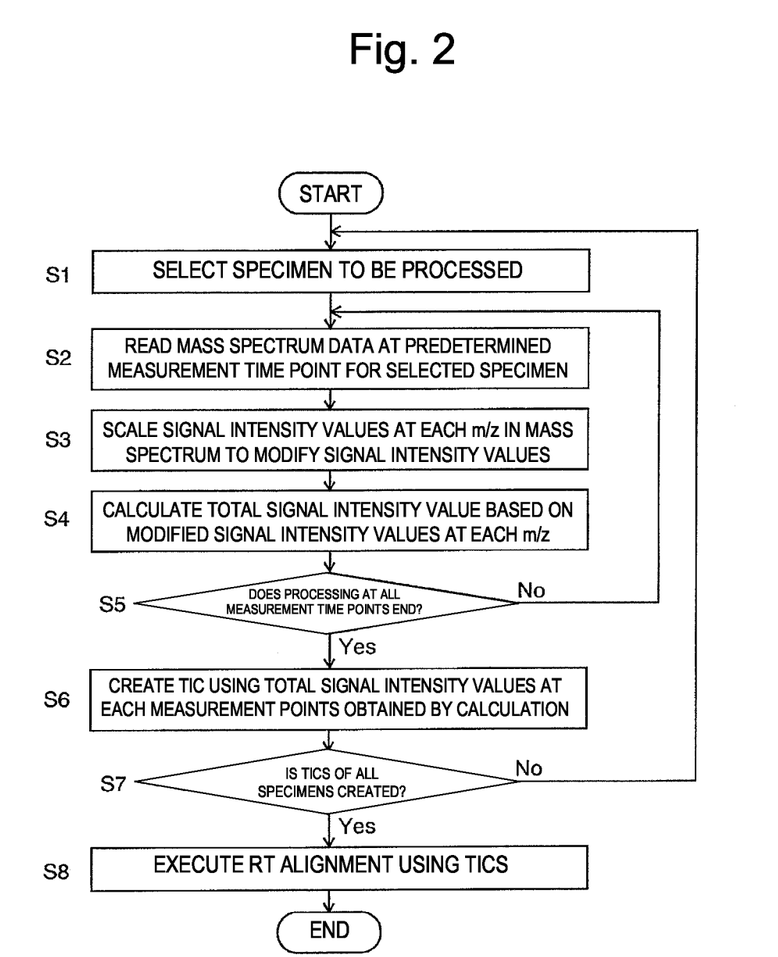
FIG. 2 is a flowchart showing the processing procedure of RT alignment processing executed in a data processing unit in the liquid chromatograph mass spectrometry system in this embodiment.

First, the mass spectrum scaling calculation unit 52 selects a specimen to be processed (for example, the specimen A) (step S1), and reads, among the three-dimensional chromatogram data for the specimen stored in the three-dimensional data storage unit 51, mass spectrum data over a predetermined mass-to-charge ratio range at a predetermined measurement time point (step S2).

Next, the mass spectrum scaling calculation unit 52 performs variable scaling on the signal intensity values of peaks detected in a mass spectrum obtained from the read mass spectrum data (or signal intensity values at mass-to-charge ratios in the mass spectrum) to modify the signal intensity values (step S3). The total signal intensity value calculation unit 53 adds the signal intensity values of peaks modified by the variable scaling in one mass spectrum to calculate a total signal intensity value at the one measurement time point (step S4).

Specifically, in this embodiment, according to a calculation formula shown in the following formula (1), variable scaling (the processing of the above step S3) and the calculation of a total signal intensity value (the processing of the above step S4) are performed.

$$TIC_{RT=t} = \Sigma(Int_i/S_{RT=t}) \cdot (<Int_{RT=t}>/S_{RT=t}) \quad (1)$$

wherein $\Sigma$ is the sum of i=1 to N, $TIC_{RT=t}$ is a total signal intensity value (a modified values by scaling) at RT=t (when the measurement time point is t), N is the number of peaks (or the number of all data points) in a mass spectrum at RT=t, i is a continuous peak number given in the mass spectrum at RT=t, $Int_i$ is the signal intensity value of the i-th peak (or data point), $S_{RT=t}$ is a standard deviation obtained from the signal intensity values of the peaks (or data points) in the mass spectrum at RT=t, and $<Int_{RT=t}>$ is the average value of the signal intensity values of the peaks (or data points) in the mass spectrum at RT=t.

The technical meaning of the above formula (1) is described.

As described above, in mass spectra obtained by a mass spectrometry apparatus using a MALDI ion source, the reproducibility of peak intensities is low, and the difference or variation in the signal intensity values of peaks at the same mass-to-charge ratio is large not only among different specimens but also among different measurement time points for the same specimen. In a TIC, the influence of peaks having high signal intensities in mass spectra is likely to appear. In other words, if a peak having an much higher signal intensity than other peaks is present in a mass spectrum, the influence of the other peaks having lower signal intensities is hidden. Therefore, if the variation or difference in the signal intensities of such peaks having relatively high signal intensities are large, the similarity in TIC waveforms among samples is low. Therefore, in order to obtain a TIC in which the low reproducibility of peak intensities is compensated for, it is necessary to perform such scaling as to suppress the influence of peaks having high signal intensities in a mass spectrum. On the other hand, because the magnitude of difference or variation in peak intensity is also a property of the mass spectrum, it is also necessary to perform scaling according to the magnitude of variation or difference in peak intensity for each mass spectrum in order to make difference in properties among mass spectra.

The first term in the sum (sigma) on the right side of the above formula (1), $(Int_i/S_{RT=t})$, is a processing in which in each mass spectrum (a mass spectrum at RT=t), the signal intensity value of the i-th peak is divided by the standard deviation of peak intensities in the mass spectrum. By this term, all variations (that is, standard deviation) in peak intensities in mass spectra are equally "1." In other words, by this first scaling, difference or variation among a plurality of mass spectra are made equal. On the other hand, the second term in the sum on the right side of the above formula (1), $(<Int_{RT=t}>/S_{RT=t})$, is obtained by dividing the average value of peak intensities in each mass spectrum by the standard deviation. This is second scaling in which the result of the above first term is weighted by variations in peak intensities present in the mass spectrum at RT=t. This second term is a processing for multiplying by the reciprocal of the coefficient variation of peak intensities in the mass spectrum at RT=t (i.e., dividing by the coefficient variation).

In other words, the operation in the sum on the right side of the above formula (1) is two-stage scaling in which the extent of variation or difference in peak intensities in each mass spectrum is scaled once so as to be equal among mass spectra, and then, further, scaling is performed again according to the magnitude of variations in peak intensity with respect to the average value of peak intensities in each mass spectrum. By such two-stage scaling, while the influence of peaks having high signal intensities in a mass spectrum is suppressed, properties that each mass spectrum has before the scaling, that is, essential variation or difference in peaks, is maintained.

The sum operation on the right side of the above formula (1) is a processing in which the signal intensity values of peaks scaled in one mass spectrum are added. Therefore, by performing the operation of the formula (1) on the signal intensity values of peaks detected in a mass spectrum, a total signal intensity value based on the scaled mass spectrum is obtained. When one total signal intensity value for a mass spectrum at certain one measurement time point is obtained, whether or not the processing at all measurement time points ends is determined (step S5). When a measurement time point at which the processing is not performed remains (No in step S5), the process returns to step S2, and mass spectrum data over the predetermined mass-to-charge ratio range at one measurement time point at which the processing is not performed is read, and the processing of steps S3 to S5 is repeated.

When total signal intensity values over the entire measurement time range for certain one specimen (for example, the specimen A) are obtained by repeating the processing of steps S2 to S5, Yes is determined in step S5, and the modified TIC creation unit 54 creates a TIC using the obtained total signal intensity values (step S6). Although not particularly specified, this is not a ordinary TIC, but is a TIC created based on scaled mass spectra.

Next, whether or not the TICs of all specimens to be processed are created is determined (step S7). When an unprocessed specimen remains (No in step S7), the process returns to step S1, and the processing of steps S2 to S7 is repeated on the unprocessed specimen. In this embodiment, after a TIC for the specimen A is created in succession, a TIC for the specimen B is created. When the TICs for all specimens to be processed are obtained, the process proceeds from step S7 to S8, and the RT alignment execution unit 55 executes RT alignment processing using the obtained TICs.

The TIC of each specimen is created based on mass spectra in which the above-described scaling as described above is performed, and therefore, the similarity in the TIC waveforms of different specimens containing substances of the same type is high. As a result, when RT alignment, for example, using dynamic programming is executed, the alignment is suitably performed, and the retention times of chromatogram peaks for the same substance are substantially aligned. In addition, among specimens in which many substances are contained in common, the TIC waveforms are similar, and therefore, an analyst can easily and appropriately determine whether or not the RT alignment is successful, while checking the TIC waveforms on the display screen of a monitor (not shown in FIG. 1), and the adjustment of the parameters of the RT alignment processing is also possible.

When the RT alignment using the TICs of two specimens ends as described above, the differential analysis unit 56 executes differential analysis based on data including the correction of the retention times, distinguishes, for example, peaks present in common in both specimens and peaks present only in any one of the specimen, and outputs the analysis results.

In addition, in the above description, the RT alignment processing using the TICs of two specimens is described, but it is also clear that RT alignment processing using the TICs of three or more specimens may be performed.

In addition, in the liquid chromatograph mass spectrometry system in the above embodiment, variable scaling is performed on a mass spectrum based on the formula (1), but variable scaling by another method can also be used.

Specifically, log scaling as represented by the following (2) formula can be used.

$$TIC_{RT=t} = \Sigma \log Int_i \quad (2)$$

wherein the definitions of $\Sigma$, $TIC_{RT=t}$, and Int, are the same as the formula (1). That is, in this formula, the logarithms of peak signal intensity values in a mass spectrum are obtained, and RT alignment is performed using total signal intensity values recalculated for each retention time. Such log scaling is scaling in which while the magnitude relationship of peaks is maintained (that is, it is reflected in a TIC at which retention times peaks having high signal intensities are present in mass spectra), the influence of peaks having high signal intensities is relatively suppressed. Thus, even when a peak having a much higher signal intensity than other peaks is present in a mass spectrum, the influence of the other peaks having lower signal intensities can be avoided from being hidden because of the peak.

EMBODIMENT

Next, experimental results for confirming the effect of RT alignment processing including the characteristic scaling of the present invention described above (scaling based on the formula (1) here), and the results of differential analysis is described together. The specimens used in the experiments here are the following two groups.

(1) "Four-protein mixture" group: A specimen obtained by mixing four proteins, that is, enolase, alcohol dehydrogenase, phosphorylase b, and bovine hemoglobin, and breaking down the proteins into peptides by a digestive enzyme.

(2) "Four-protein mixture+BSA" group: A specimen obtained by adding, to the four proteins used in the above "four-protein mixture" group, an additional protein "bovine serum albumin," and breaking down the proteins into peptides by a digestive enzyme. In the following description, bovine serum albumin is abbreviated as BSA.

When differential analysis between these two groups is performed, and peaks that are not present in the "four-protein mixture" group and are present in the "four-protein mixture+BSA" group are identified as the peaks of BSA or the peptide derived from BSA, it can be concluded that the RT alignment is suitable and the differential analysis is accurately performed.

Figure 3:
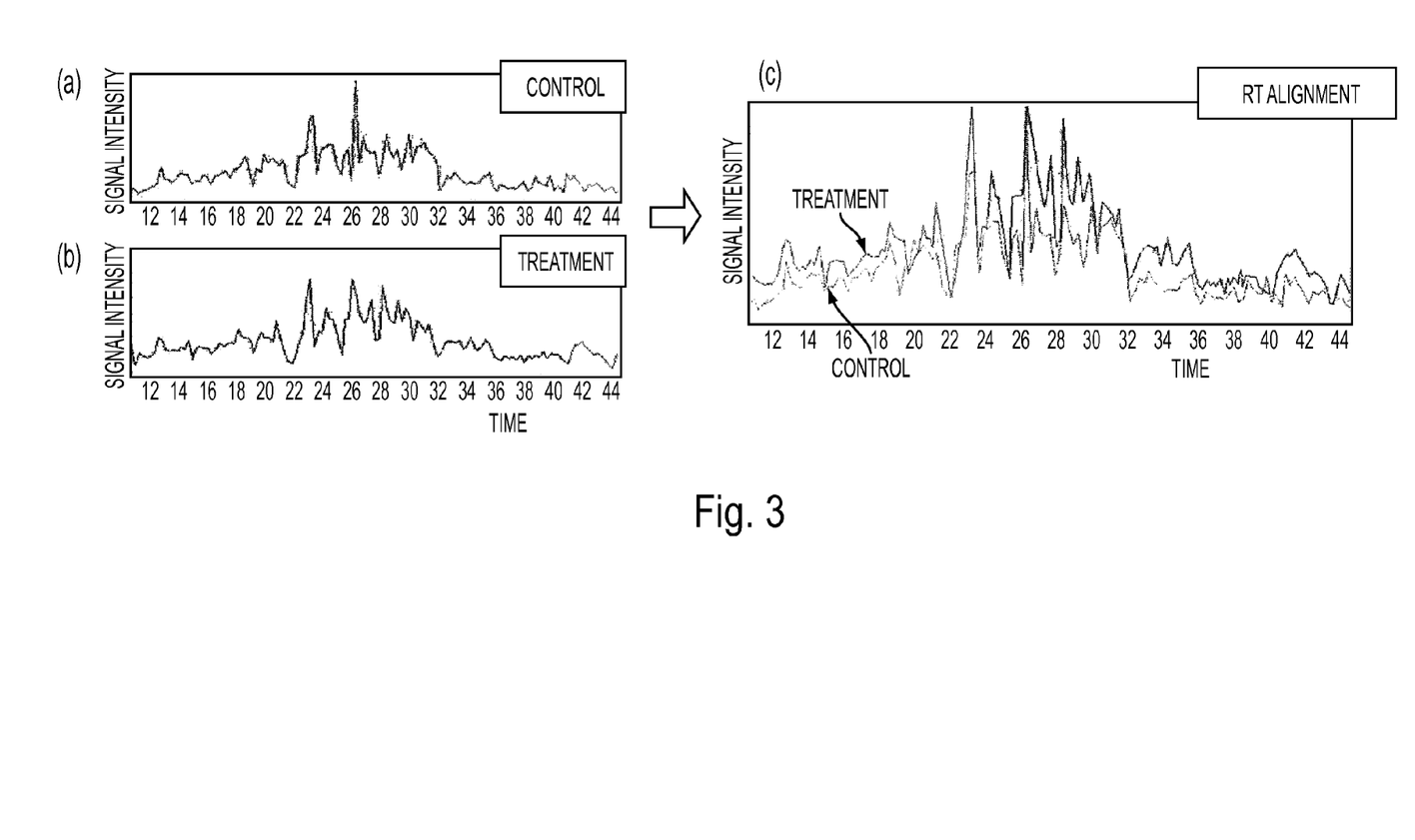
FIG. 3 shows individual TIC waveforms when scaling on a mass spectrum is not carried out, and one example of a graph in which they are overlapped.

FIGS. 3(a) and 3(b) are TICs without scaling on two specimens, and FIG. 3(c) is a graph in which both TICs after RT alignment is executed using the TICs are overlap-displayed. The specimens used here are two specimens belonging to the "four-protein mixture+BSA" group, and for convenience, one is regarded as "Control," and the other is regarded as "Treatment." At the point before the RT alignment is executed, the similarity between the TIC waveform of the Control and the TIC waveform of the Treatment is low. Therefore, even if the RT alignment is performed, the peak tops, the peak bottoms, the peak widths, and the like do not match, and it is difficult to determine whether or not the RT alignment is successful. The parameters of the RT alignment at this time are the same as the parameters of RT alignment in FIG. 4 described later.

Figure 4:
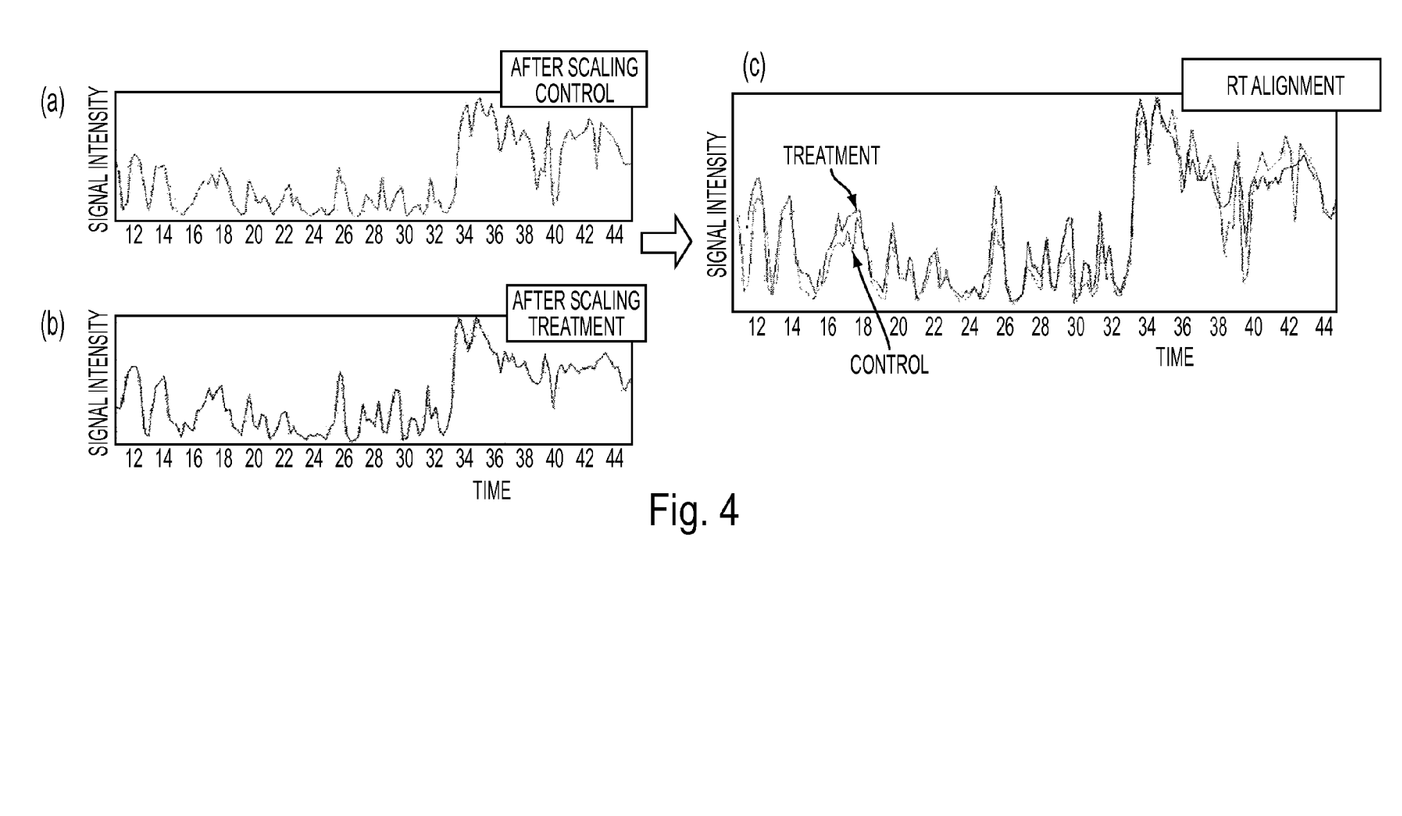
FIG. 4 shows individual TIC waveforms when scaling on a mass spectrum is carried out, and one example of a graph in which they are overlapped.

FIGS. 4(a) and 4(b) are TICs obtained by calculation after the above-described characteristic scaling is applied to data obtained from the same specimens as FIG. 3, and FIG. 4(c)

is a graph in which both TICs after RT alignment is executed using the TICs are overlap-displayed. As found by seeing FIGS. 4(a) and 4(b) (particularly comparing them with FIGS. 3(a) and 3(b)), at the time point before the RT alignment is executed, the similarity between the TIC waveform of the Control and the TIC waveform of the Treatment is quite high. In addition, after the RT alignment is performed, the peak tops, the peak bottoms, the peak widths, and the like match well, and therefore, it can be determined that the RT alignment is successful. This FIG. 4(c) shows the results when an analyst adjusts the parameters of the RT alignment and visually determines that the RT alignment is most successful.

From the above experimental results, it can be confirmed that by the chromatograph mass spectrometry data processing apparatus according to the present invention, even when the reproducibility of peak intensities observed in mass spectra is low, whether or not the RT alignment is successful can be determined from TIC waveforms, and parameter adjustment in the RT alignment is also possible.

Figure 5A:
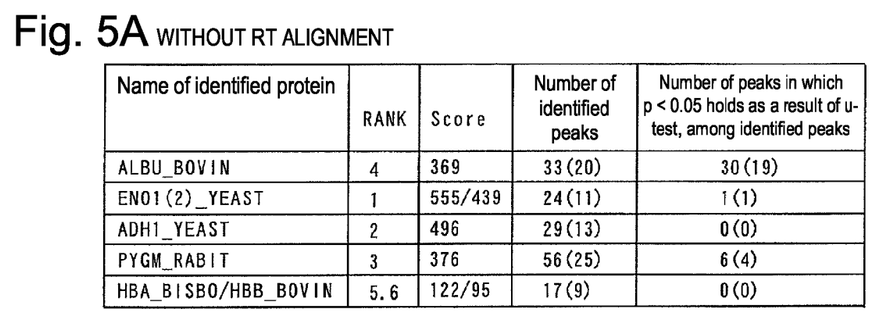
FIGS. 5A through 5C show one example of the results of identification processing and differential analysis on specimens that are mixtures of a plurality of proteins.
Figure 5B:
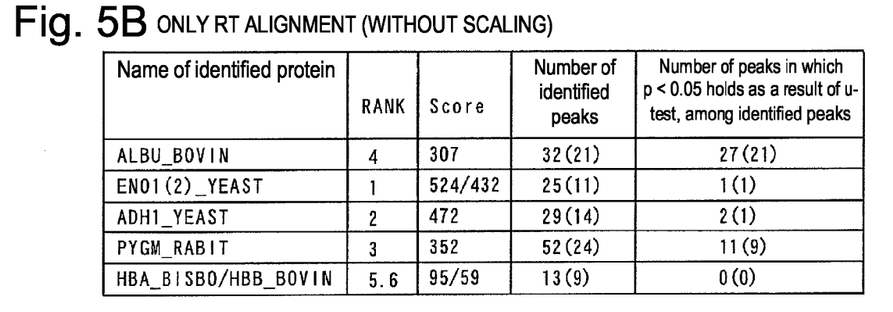
Figure 5C:
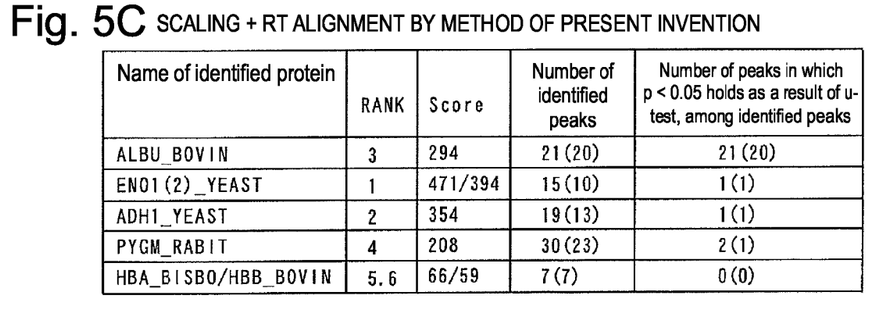

FIGS. 5A through 5C show the results of applying the RT alignment processing performed in FIG. 3 and FIG. 4 to other specimens, and performing identification processing and differential analysis. In this experiment, five specimens belonging to the "four-protein mixture" group, and four specimens belonging to the "four-protein mixture+BSA" group were used. FIG. 5A shows the results of performing identification processing and differential analysis without performing the RT alignment at all. FIG. 5B shows results when the RT alignment is executed without scaling (that is, when conventional general RT alignment is executed). FIG. 5C shows results when the present invention is applied (that is, when the RT alignment is executed after the above-described characteristic scaling is carried out).

In FIGS. 5A through 5C, "RANK" and "Score" are presented in search results in database search using Mascot manufactured by Matrix Science Inc. in the United States, which is frequently used for protein identification. In these search results, ENO1(2)_YEAST corresponds to enolase, ADH1_YEAST corresponds to alcohol dehydrogenase, PYGM_RABIT corresponds to phosphorylase b, HBA_ISBO/HBB_BOVIN corresponds to bovine hemoglobin (the protein contained in the specimens was bovine hemoglobin, but was identified as "HBA_BISBO or HBB_BOVIN," meaning that peptides constituting both proteins were very similar, and could not be distinguished), and ALBU_BOVIN (=BSA) corresponds to bovine serum albumin. In addition, "Number of identified peaks" and "Number of peaks in which p<0.05 holds as a result of u test, among identified peaks" are each the number of peaks identified as "the peaks of the peptide derived from the protein" in mass spectra for all specimens (nine specimens here). In these, a numerical value within parentheses is the number of peaks excluding redundant peaks. The "redundant peaks" here have the meaning as described below.

Figure 6A:
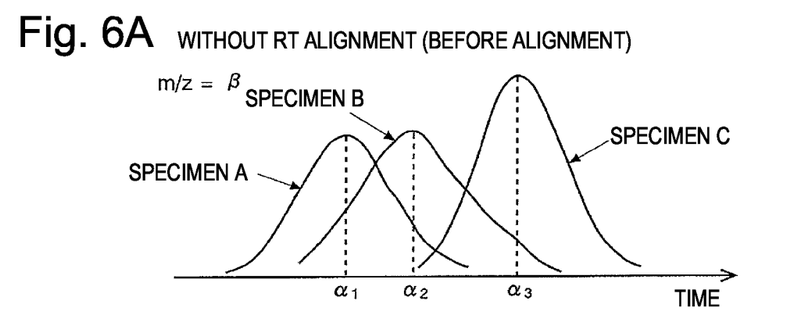
FIGS. 6A and 6B show schematic diagrams for explaining the effect of RT alignment processing according to the present invention.

When RT alignment is not performed for TICs obtained from different specimens, even for chromatogram peaks derived from the same substance (peptide here), peaks are often observed at different times among specimens. FIG. 6A shows one example thereof, and a peak derived from the same substance with a mass-to-charge ratio m/z of $\beta$ has a peak top at $RT=\alpha_1$ for a specimen A, at $RT=\alpha_2$ for another specimen B, and at $RT=\alpha_3$ for an another specimen C. In such a case, although being essentially the same peak, a plurality of peaks are erroneously detected. Therefore, peaks that are essentially one peak but are seen as a plurality of peaks in this manner are referred to as "redundant peaks" here. In FIG. 6A, the essential peak is one, and therefore, two redundant peaks are present.

Figure 6B:
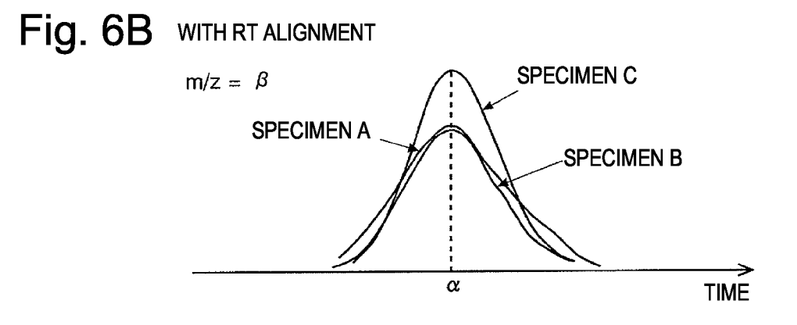

On the other hand, when RT alignment is suitably performed, peaks derived from the same substance are corrected so as to appear in the TICs of all specimens at the same time. In other words, as shown in FIG. 6B, all the peak tops of peaks derived from the same substance appear at $RT=\alpha$. In this case, no redundant peaks are present. In this manner, when RT alignment is suitably performed, it is expected that redundant peaks decrease or disappear. In other words, when the decrease or disappearance of redundant peaks can be confirmed, this means that RT alignment is suitably performed.

To be precise, a state in which no redundant peaks are present is a state in which the times of the peak tops of peaks derived from the same substance overlap completely among a plurality of specimens (that is, in FIG. 6B, the appearance times of the peak tops of all peaks are $\alpha$). But, actually, due to various error factors and variations, it is difficult to achieve such a state. Therefore, it is good to previously determine a moderate allowable range for the appearance times of peak tops and, when the appearance times of the peak tops of peaks fall within the allowable range, determine that no redundant peaks are present.

In addition, here, whether or not there are peaks that are not present in the "four-protein mixture" group and are present in the "four-protein mixture+BSA" group is determined by a p value, a statistic. Specifically, in a case where the area values (or signal intensity values or the like) of the peaks at the positions (RT, m/z) of the peaks are compared between the groups, when the p value is less than 0.05, then it is determined that the possibility that there is a difference between the groups is high.

The object of the differential analysis in this experiment is to identify a peptide that is a biomarker, or narrow down candidates for the peptide. Therefore, the number of redundant peaks for peaks derived from a peptide, which are erroneously determined to have a difference between the groups, or which are not clearly determined whether to have a difference between the groups, is preferably smaller, and ideally, the number of redundant peaks should be zero. Of course, even if the number of redundant peaks can be decreased using some method, this is meaningless when due to this, the number of identified peptides (that is, the number of peaks excluding redundant peaks from all identified peaks) decreases largely. In other words, preferably, with a least decrease in the number of peaks excluding redundant peaks from all identified peaks, the number of redundant peaks is decreased or made zero. In addition, the number of peaks that are, although being peaks derived from a common peptide, erroneously determined to be "different" between both groups is preferably smaller, and should be ideally zero.

In summary, when the RT alignment is successful, the identification processing and differential analysis results shown in FIGS. 5A through 5C are expected to be as follows.

(A) For all proteins, the number of redundant peaks decreases. In other words, the number of peaks outside parentheses and the number of peaks within the parentheses in the column "Number of identified peaks" are close to each other.

(B) For ALBU_BOVIN (=BSA) contained only in the "four-protein mixture+BSA" group, the number of redundant peaks (the difference between the number of peaks outside parentheses and the number of peaks within the parentheses) in the column "Number of peaks in which p<0.05 holds as a result of u test, among identified peaks" decreases.

(C) For ALBU_BOVIN (=BSA), "Number of identified peaks" and "Number of peaks in which p<0.05 holds as a result of u test, among identified peaks" are close or equal to each other. In other words, most or all of identified peaks are determined to be "different" between the groups.

(D) For ALBU_BOVIN (=BSA), in FIG. 5C, the number of identified peptides does not decrease largely compared with those in FIGS. 5A and 5B.

(E) For the proteins (four proteins) present in common in both groups, "Number of peaks in which p<0.05 holds as a result of u test, among identified peaks" decreases. In other words, the proteins present in common being erroneously determined to be present only in one group decreases.

From the viewpoints as described above, seeing the results in FIGS. 5A through 5C, the following can be said.

Now, seeing the column "Number of identified peaks" in FIG. 5B, the number of all peaks identified as "ALBU_BOVIN" (=BSA) is 32, and when redundant peaks within a previously determined allowable range as described above are excluded, the number of peaks is 21. This indicates that quite many redundant peaks are present, that is, chromatogram peaks derived from the same peptide appear at different positions of the retention time. In addition, when FIGS. 5A and 5B are compared, there is not so large difference seen. In other words, no large difference in results is seen between RT alignment without scaling and No RT alignment, and it can be concluded that in performing differential analysis, RT alignment without scaling is not very effective.

On the other hand, when FIGS. 5A and 5C are compared, a significant decrease in redundant peaks is seen in all of the five proteins. In other words, the above (A) is realized. In addition, the number of redundant peaks in "Number of peaks in which p<0.05 holds as a result of u test, among identified peaks" derived from ALBU_BOVIN (=BSA) decreases sharply from "11" to "1," and the above (B) is also realized. In addition, "Number of identified peaks" and "Number of peaks in which p<0.05 holds as a result of u test, among identified peaks" derived from ALBU_BOVIN (=BSA) are equal to each other, and (C) is also realized. Further, "Number of peaks in which p<0.05 holds as a result of u test, among identified peaks" derived from the protein "PYGM_RABIT," which is relatively large, "6(4)," in FIG. 5A decreases significantly to "2(1)" in FIG. 5C. In other words, the above (E) is also realized. Further, "Number of identified peaks" derived from ALBU_BOVIN (=BSA) excluding redundant peaks is almost unchanged. This number of peaks is considered to correspond to the number of peptides, and therefore, the above (D) is also realized.

From the above, it can be concluded that in this experiment example, the RT alignment can be properly executed, and the superiority of the RT alignment processing with the characteristic scaling in the present invention can be confirmed.

Here, mixtures of proteins are used as specimens. But, as described above, the RT alignment processing specific to the present invention does not use the properties and specificity of proteins and peptides, and therefore, it is clear that the application of the RT alignment processing of the present invention is not limited to proteins and peptides, and the RT alignment processing of the present invention can be applied to any type of specimen.

In addition, the above embodiment is only one example of the present invention, and of course, any appropriate changes, modifications, additions, and the like made without departing from the spirit of the present invention will fall within the scope of the appended claims of this application.

EXPLANATION OF NUMERALS

1 . . . Liquid Chromatograph Unit
2 . . . Spotting Unit
3 . . . Mass Spectrometry Unit
31 . . . MALDI Ion Source
32 . . . TOF Mass Separation Unit
33 . . . Detector
4 . . . Analog-Digital Converter
5 . . . Data Processing Unit
51 . . . Three-Dimensional Data Storage Unit
52 . . . Mass Spectrum Scaling Calculation Unit
53 . . . Total Signal Intensity Value Calculation Unit
54 . . . Modified TIC Creation Unit
55 . . . RT Alignment Execution Unit
56 . . . Differential Analysis Unit

The invention claimed is:

1. A chromatograph mass spectrometry data processing apparatus for processing data collected by a chromatograph mass spectrometry apparatus, the data processing apparatus performing alignment processing for correcting a shift in retention time in a plurality of chromatograms obtained from data obtained for a plurality of specimens, and comprising:
   a) a mass spectrum scaling processing unit for scaling signal intensities in a mass spectrum created, for each measurement time point within an entire measurement time range or within part of the measurement time range, based on data obtained at the measurement time point;
   b) a total signal intensity value calculation unit for calculating, for each of the mass spectrum, a total signal intensity value obtained by adding signal intensity values after being scaled by the mass spectrum scaling processing unit;
   c) a chromatogram creating unit for creating, for each of a plurality of specimens, a total ion chromatogram from a plurality of total signal intensity values calculated by the total signal intensity value calculation unit; and
   d) an alignment execution unit for executing alignment processing using a plurality of chromatograms created by the chromatogram creating unit.

2. The chromatograph mass spectrometry data processing apparatus according to claim 1, wherein
   the mass spectrum scaling processing unit performs variable scaling combining first scaling and second scaling, where the first scaling is for equalizing or at least reducing an extent of variations in signal intensity values in one mass spectrum, among different mass spectra, and the second scaling is for performing weighting according to relative variations in signal intensity values for each mass spectrum.

3. The chromatograph mass spectrometry data processing apparatus according to claim 2, wherein
   the first scaling is a processing for dividing by a standard deviation of signal intensities of peaks in the mass spectrum, and the second scaling is a processing for multiplying by a value obtained by dividing an average value of the signal intensities of the peaks in the mass spectrum by the standard deviation.

4. The chromatograph mass spectrometry data processing apparatus according to claim 1, wherein the mass spectrum scaling processing unit performs scaling processing for taking logarithms of signal intensities of peaks in one mass spectrum.

\* \* \* \* \*